United States Patent
Cole

(10) Patent No.: US 7,315,175 B2
(45) Date of Patent: Jan. 1, 2008

(54) PROBE APPARATUS AND METHOD FOR EXAMINING A SAMPLE

(75) Inventor: Bryan Edward Cole, Cambridge (GB)

(73) Assignee: TeraView Limited (GB)

( * ) Notice: Subject to any disclaimer, the term of this patent is extended or adjusted under 35 U.S.C. 154(b) by 0 days.

(21) Appl. No.: 10/470,836

(22) PCT Filed: Jan. 30, 2002

(86) PCT No.: PCT/GB02/00432

§ 371 (c)(1),
(2), (4) Date: Dec. 11, 2003

(87) PCT Pub. No.: WO02/061398

PCT Pub. Date: Aug. 8, 2002

(65) Prior Publication Data

US 2004/0095147 A1    May 20, 2004

(30) Foreign Application Priority Data

Jan. 30, 2001    (GB) ................................ 0102345.6

(51) Int. Cl.
*G01R 31/305*    (2006.01)
(52) U.S. Cl. .................... 324/751; 324/750; 324/752
(58) Field of Classification Search .................... None
See application file for complete search history.

(56) References Cited

U.S. PATENT DOCUMENTS

| | | | | |
|---|---|---|---|---|
| 4,841,234 A | * | 6/1989 | Aoshima et al. | 324/96 |
| 5,406,194 A | * | 4/1995 | Dykaar et al. | 324/96 |
| 5,475,489 A | * | 12/1995 | Gottsche | 356/364 |
| 5,912,456 A | * | 6/1999 | Melendez et al. | 250/216 |
| 6,369,562 B2 | * | 4/2002 | Ito et al. | 324/96 |

FOREIGN PATENT DOCUMENTS

| | | |
|---|---|---|
| EP | 0 032 774 | 7/1981 |
| EP | 0 047 094 | 3/1982 |
| EP | 0 126 031 | 11/1984 |
| EP | 0 232 802 | 8/1987 |
| GB | 2 017 899 | 10/1979 |
| GB | 2 060 164 | 4/1981 |
| GB | 2 352 512 | 1/2001 |
| JP | 11-23457 | 1/1999 |
| JP | 11-271217 | 10/1999 |
| JP | 11-287754 | 10/1999 |
| JP | 11-287868 | 10/1999 |
| JP | 11-295214 | 10/1999 |
| WO | WO 00/75641 | 12/2000 |

* cited by examiner

*Primary Examiner*—Minh N. Tang
(74) *Attorney, Agent, or Firm*—Ostrolenk, Faber, Gerb & Soffen, LLP

(57) ABSTRACT

A probe for examining a sample (5), the probe including an emitter (1) for emitting radiation, a detector (1) for detecting radiation and a dielectric member (3) configured to direct radiation from the emitter (1) to the sample (5) and to direct radiation reflected by the sample (5) to the detector (1), wherein in use, the dielectric member (3) occupies at least half of the radiation path length from the emitter (1) to the sample (5) to the detector (1).

18 Claims, 9 Drawing Sheets

PROBE APPARATUS AND METHOD FOR EXAMINING A SAMPLE

BACKGROUND OF THE INVENTION

The present invention relates generally to the field of probes, apparatus and methods for investigating or examining samples. More specifically, the present invention relates to a probe which comprises a dielectric body which can be used to direct light from the probe onto the sample and/or collect light from the sample into the probe. The present invention also relates to apparatus such as transceivers, which may be used with such probes. The present invention is primarily intended for use in the frequency range 25 GHz to 100 THz. This frequency range is colloquially referred to as the THz range.

There has been much interest in using THz radiation to look at a wide variety of samples using a range of methods. THz radiation has used for both imaging samples and obtaining spectra. Recently, work by Mittleman et al, IEEE General Selective Topics in Quantum Electronics, Volume 2, No. 3, September 1996, page 679 to 692 illustrates the use of THz radiation to image various objects such as flame, a leaf, a moulded piece of plastic and semiconductors.

THz radiation penetrates most dry, non-metallic and non-polar objects like plastics, paper, cardboard and non-polar organic substances. Therefore, THz radiation can be used instead of X-rays to look inside boxes, cases, etc. THz photons are lower energy than those of X-rays and are non-ionising. Therefore, the health risks of using THz radiation are expected to be vastly reduced compared to those using conventional X-rays.

There is a need to develop a probe which can be used to either emit or detect THz radiation. Preferably, the probe is configured to both emit and detect THz radiation.

Previously, probes using THz radiation have included Lai et al Appl. Phys. lett. 69 1843 (1996). In this paper, a photo-conductive-sampling probe is fabricated from low-temperature-grown GaAs. The probe is mounted on a single mode optical fibre. The photo-conductive sampling probe is used to detect radiation. A later paper by Lai et al in Appl. Phys. lett. 72 3100 (1998) discusses a micro-machined photo-conductive THz emitter which is formed from low-temperature-grown GaAs mounted on a pair of single mode optical fibres.

The above two papers demonstrate that it is possible to use a fibre optic THz probe to emit THz or detect THz. However, no consideration is given to what happens to the THz radiation once it is generated or how the THz beam actually arrives at the detector.

Fattinger et al in Appl. Phys. lett. 53 1480 (1998) demonstrates simultaneous emission and detection of a THz beam using a silicon on sapphire photo-conductive device and a solid hemispherical Sapphire mirror. In a slightly later publication, Appl. Phys. lett. 44 490 (1989), the same research group demonstrates transmission of a THz beam from a separate emitter to a separate detector. Both the emitter and detector use solid hemispherical sapphire lenses. However, there is no disclosure of how to direct the beam onto a sample or from a sample.

Although, the field of geometrical optics is well developed for radiation of certain wavelengths, different and extra restrictions apply when developing a probe which can operate with THz radiation. None of the above documents address the problem of the different absorption and propagation characteristics of THz radiation.

BRIEF SUMMARY OF THE INVENTION

In a first aspect, the present invention provides a probe for examining a sample, the probe comprising an emitter for emitting radiation, a detector for detecting radiation and a dielectric member configured to direct radiation from the emitter to the sample and to direct radiation reflected by the sample to the emitter, wherein in use, the dielectric member occupies at least half of the radiation path length from the emitter to the sample to the detector.

The dielectric member is preferably a solid dielectric member which can also provide structural rigidity to the probe. The dielectric member directs the radiation by refracting or internally reflecting the radiation and preferably, a combination of the two.

According to a second aspect, the present invention provides a probe for examining a sample, the probe comprising an optically active element for emitting and/or detecting radiation and a dielectric body for directing radiation between the sample and the active element, wherein the dielectric body provides substantial structural rigidity to the probe.

A single element which can perform a number of optical operations has been previously suggested in U.S. Pat. No. 5,995,287. Here, the optic is used instead of a number of passive optical elements in a video camera or the like. However, in this document, there is no disclosure of how much of the total optical path length this solid optic should occupy.

In the present invention, the radiation path length outside the dielectric medium should be minimised. Preferably the medium occupies at least 75% of the radiation path length, more preferably at least 90%, even more preferably 95%.

The dielectric medium will have a higher refractive index than free space, thus, it can also server to reduce the spot size of the beam of radiation and hence allow greater resolution.

Preferably, the emitter is located such that radiation passes from the emitter to the dielectric member without passing through free space or an air gap. To achieve this, the emitter may abut against a surface of the dielectric member such that radiation passes from the emitter to the dielectric member without passing through free space or an air gap. Alternatively, a non-rigid medium other than air or free space may be interposed between the emitter and the dielectric member.

Also, preferably, the detector is located such that radiation passes from the dielectric member to the detector without passing through free space or an air gap. This may be achieved by abutting the detector against a surface of the dielectric member or by providing a non-rigid medium other than air or free space interposed between the detector and the dielectric member.

The emitter and detector may be spatially separated from one another or may be integral with one another to form a transceiver. The transceiver is preferably located as described for the emitter and detector above.

The dielectric member does not have to be a continuous piece of material. It may comprise a plurality of different sections which may be detachable from and attachable to one another. The different sections may be of the same material or may comprise different materials. The dielectric member may comprise an emitter joining section which abuts against the emitter, a detector joining section, which abuts against the detector or a transceiver joining section which abuts against the transceiver.

In order to correctly align the optics, it is preferable if the emitter and/or detector is mounted on the dielectric member.

In general, the dielectric member will be much larger than the emitter, detector or transceiver.

For example, the detector may be provided with at least one projection and/or recess and the surface which it abuts may be provided with at least one complementary projection and/or recess such that the detector can be rigidly connected to the dielectric member. Also, the emitter may be provided with projections and/or recesses and the surface which it abuts may be -provided with complementary projections and/or recesses such that the emitter can be rigidly connected to the dielectric body.

The idea of mounting the active optical elements, e.g. the transceiver, detector or emitter on the dielectric itself can be used for any system which uses such a member and the member is of a sufficient size to support the active optical elements.

Therefore, in a third aspect, the present invention provides a probe for examining a sample, the probe comprising an active optical element for emitting and/or detecting radiation and a dielectric member for transmitting the radiation between the sample and the active element, wherein active element is mounted on the dielectric member.

Although it is possible to fix the position of the active elements of the probe with respect to the dielectric member, the position of the dielectric member with respect to the sample cannot be so well defined. The sample is preferably provided at the focal point of the probe for both the emitter and detector. Preferably, the emitter and detector are located at a focal points of the dielectric member and the sample is located at a corresponding focal point of the dielectric member. For example, if the dielectric member is ellipsoidal, the emitter and detector can be provided at one of focus of the ellipsoid and the sample can be positioned at the other focal point of the ellipsoid. The ellipsoid is preferably truncated at its 'ends' in order to accommodate the sample and the active elements at its foci.

The dielectric member preferably has a probing surface through which radiation from the emitter exits the probe to irradiate the sample and radiation reflected from the sample enters the probe. In order to minimise the amount of free space or air through which the radiation passes, the probing surface is preferably configured to abut against the sample under investigation. In this situation, the sample focal point is provided on the probing surface.

Alternatively, a non-rigid medium other than free space or an air gap is interposed between the sample and the probing surface. In this situation, the focal point is preferably designed to be external from the dielectric medium in order to compensate for the thickness of the non-rigid medium.

The part of the dielectric member which contacts the sample may need to be replaced for possible hygiene reasons and also because it will suffer from general wear and tear. Preferably, the dielectric medium comprises a tip section which is provided at the sample end of the dielectric medium. More preferably, the tip section is configured to be disengaged and re-engaged from the remainder of the dielectric medium so that it can be replaced by an identical tip if necessary.

Often, it will be necessary to examine samples which have non-planar surfaces, for example, teeth. In this type of situation, it is preferable to have a tip which can deform to the shape of the sample. One such tip comprises a non-rigid balloon comprising a liquid or gas. Preferably, the balloon material is polythene and the fluid is chosen from silicone fluid, silicone rubber, mineral oil or wax.

It has been previously mentioned that the dielectric member is configured to direct the radiation by internally reflecting the radiation within the member.

To achieve this, the dielectric member preferably comprises at least one surface which forms at least a part of a substantially ellipsoidal surface, and wherein the probe is configured such that the said surface is used to internally reflect radiation within the dielectric member. The ellipsoidal surface allows all of the frequency components of the pulsed radiation to be focused at the same point, a focus of the ellipse.

It is particularly preferable if the dielectric member is substantially ellipsoidal as the calculation of the focal points is simpler. However as the probe has a separate emitter and detector, it is preferable if the dielectric member has at least two surfaces which form at least a part of a substantially ellipsoidal surface, wherein the emitter and detector are located at a focal point for each the ellipsoids defined by the partial surfaces.

Metalised surfaces may be provided for internally reflecting the radiation within the dielectric member.

The dielectric member may also be used to direct the radiation using refraction. This may be done in addition to or instead of internally reflecting the radiation. In order to direct the radiation within the dielectric medium, the medium comprises at least two dielectric sections have differing refractive indices.

More preferably, the dielectric member comprises first, second and third sections, arranged such that radiation emitted from the emitter passes through the first section, then the second section and then the third section prior to irradiating the sample.

For example, the second section may be biconcave in shape and oriented to allow radiation to enter the second section though one concave surface and exit through the other concave surface, the refractive index of the second section being lower than the refractive index of the first and third sections.

In an alternative arrangement, the second section is biconvex in shape and is oriented such radiation enters the second section though one convex surface and exits through the other convex surface, the refractive index of the second section being higher than the refractive index of the first and third sections.

The second section may be formed from one chosen from polythene, paraffin wax, silicone, silica, TPX or polypropylene. Alternatively, the second section may comprise a container and a non-rigid material provided within the container. The non-rigid material may be chosen from silicone grease, silicone fluid or liquid paraffin. The container does not have to lie in the path of the THz radiation and any manufacturable material can be used. If the container lies in the path of the THz beam, it preferably comprises polythene, propylene, mylar, TPX or any material which is substantially transparent to THz radiation.

In general, the dielectric member will be solid and preferably comprises crystalline silicon, amorphous silicon, amorphous germanium, crystalline germanium, quartz, sapphire, diamond, high density polythene, TPX or alumina. The above materials can also be used for a section of the probe such as the tip section of the first, second and third sections referred to above.

In a fourth aspect, the present invention provides a probe for examining a sample, the probe comprising an active optical element for emitting and/or detecting radiation and a dielectric member for transmitting the radiation between the sample and the active element, wherein the member comprises at least two sections having different refractive indices.

The probe of the present invention is primarily intended for use in the THz frequency range. Therefore, preferably, the emitter is configured to emit radiation having at least one frequency in the range from 25 GHz to 100 THz. More preferably, the emitter emits pulsed THz radiation, therefore, the emitter is preferably configured to emit pulses of radiation having a plurality of frequencies, at least one of said frequencies being in the range from 25 GHz to 100 THz.

There is no naturally occurring source of THz radiation. However, it-is possible to directly generate THz radiation using Gunn diodes and also cascade lasers. In order to produced pulsed THz radiation the emitter may comprise a frequency conversion member which is configured to emit radiation of the desired frequency in response to irradiation by radiation having a different frequency. Generally, the frequency conversion member is configured to emit radiation which is the difference of the frequency of two input beams. To generate THz radiation, a pulsed (i.e. plurality of frequencies) input beam can be used whose frequencies lie in the near infra-red part of the spectrum.

Photoconductive devices (see for example U.S. Pat. No. 5,729,017) can also be used to generate THz radiation, here the emitter comprises a photo-conductive material and an electrode configured to apply a bias across the photoconductive material, the photoconductive material being configured to emit radiation of the desired frequency in response to irradiation by a pump beam of radiation having at least two frequency components with frequency different to the desired frequency.

A similar detector would comprise a photo-conductive material and an electrode configured to measure a current flowing through the photo-conductive material, the photoconductive material being configured to generate a current in response to irradiation by a both a probe beam comprising at least two frequency components and a beam of radiation having the frequency which is to be detected.

The structure of a photoconductive emitter and a photoconductive detector as essentially the same and the same device can be used to provide both functions, providing that it is switched between providing a bias across the electrodes for THz emission and measuring the current between the electrodes for THz detection. It is possible to fabricate a device based on the photoconductive principle which can both emit and detect.

Therefore, the probe is preferably provided with a transceiver which comprises a planar electrode and two mutually separated first and second photoconducting members, the electrode comprising a main section and first and second separated sections located on either side of the main section such that a first gap is formed between the main section and the first separated section and a second gap is formed between the main section and the second separated section, wherein the first photoconductive member bridges at least part of the first gap and the second photoconducting member bridges at least part of the second gap, wherein a bias can be applied across the surface of the first photoconducting member to act as an emitter of radiation and a current can be measured through the second photoconductive material to act as a detector.

In a fifth aspect, the present invention provides a transceiver comprising a planar electrode and two mutually separated first and second photoconducting members, the electrode comprising a main section and first and second separated sections located on either side of the main section such that a first gap is formed between the main section and the first separated section and a second gap is formed between the main section and the second separated section, wherein the first photoconductive member bridges at least part of the first gap and the second photoconducting member bridges at least part of the second gap, wherein a bias can be applied across the surface of the first photoconducting member to act as an emitter of radiation and a current can be measured through the second photoconductive material to act as a detector.

Preferably, the electrode is configured such that it has a waist, the first photoconducting member being located on one side of the waist being configured as an emitter and the second photoconducting member being located on the other side of the waist being configured as a detector. In this configuration, it is possible to generate and detect THz radiation at exactly the same point on the transceiver.

Preferably, the first gap extends from the waist and the first photoconducting member is located remote from the waist such that radiation emitted by the first photoconducting member propagates along the first gap and is emitted at the waist, the second gap also extending from the waist and the second photoconducting member being located remote from the waist such that radiation incident on the waist propagates along the second gap to the second photoconductive member for detection.

Other types of transceiver may also be used, for example a hybrid type of transceiver which uses photoconductive effects to detect the radiation and non-linear optical effects to detect radiation or vice versa.

Thus in a sixth aspect, the present invention provides a transceiver comprising a photoconductive member for emitting emitted radiation upon application of a bias and in response to irradiation by a pump beam of radiation having a different frequency to that of the emitted radiation, the transceiver further comprising an optically non-linear member configured to detect a beam of detected radiation by modifying a probe beam which irradiates said non-linear member with said detected radiation.

In a seventh aspect, the present invention provides a transceiver comprising a photoconductive member configured to detect detected radiation by generating a current in response to irradiation by both the detected radiation and a probe beam of radiation having a different frequency to that of the detected radiation, the transceiver farther comprising an optically non-linear member configured to emit emitted radiation in response to irradiation by a pump beam of radiation having a different frequency to that of the emitted radiation.

As this type of transceiver is intended to be used to emit THz radiation, the emitted radiation and the detected radiation will be assumed to be THz radiation. However, it should be appreciated that other types of radiation can also be used with this type of transceiver.

Preferably an electrode is provided to apply a bias to the photoconductive member (if it is acting as an emitter) or to detect a current flowing through the photoconductive member (if it is acting as a detector). This electrode is also preferably configured as an antenna such that it also serves to concentrate detected radiation at a predefined region of the transceiver and to emit radiation from the same region of the transceiver regardless of whether the radiation is emitted (or detected) by the non-linear member or the photoconductive member.

Generally, the transceiver will be provided on a substrate. The emitted THz radiation will always be emitted into the region having the highest refractive index, and will generally be emitted into the substrate.

The optically non-linear member may be provided on either side of the photoconductive member. However, preferably the photoconductive member and non-linear member are arranged such that the pump beam or probe beam impinges on the non-linear member before the photoconducting member as the photoconducting member will absorb the pump and probe beams.

Alternatively, a single member maybe provided which exhibits both non-linear and photoconductive effects, the member being configured to emit radiation using the photoconductive effect detect radiation using non-linear optical effects or vice versa.

Thus, in an eighth aspect, the present invention provides a transceiver comprising a member which exhibits both photoconductive and non-linear properties, the member being configured to detect detected radiation by generating a current in response to irradiation by both the detected radiation and a probe beam of radiation having a different frequency to that of the detected radiation and being configured to emit emitted radiation in response to irradiation by a pump beam of radiation having a different frequency to that of the emitted radiation.

In a ninth aspect, the present invention provides a transceiver comprising a member which exhibits both photoconductive and non-linear properties, the member being configured to emit emitted radiation in response to irradiation by a pump beam of radiation having a different frequency to that of the emitted radiation and upon application of a bias; and being configured to detect detected radiation by modifying a probe beam irradiating said non-linear member with said detected radiation.

A suitable electrode may comprise two pointed sections, the transceiver being configured such that a bias is applied between the nearest two points of the pointed sections. A so-called 'bow-tie' shaped electrode is an example of such an arrangement. However, electrodes of any arrangement may be used, for example a dipole arrangement, a double dipole arrangement or a transmission line arrangement as described in Fattinger et al. Appl. Phys. Lett. 54 4901 (1989).

These types of electrodes may also be used for the previously described transceivers, detectors and emitters, including those which only operate using photoconductive properties.

Typical examples of materials which can be used as both the photoconducting member and the optically non-linear member are GaAs or any III-V or II-VI material.

In each of the above described transceivers, emitters and detectors, the use of a pump beam and/or probe beam has been described. Generally, the pump beam will be a pulsed beam comprising at least two frequency components, the emitted radiation having a frequency substantially equal to the difference of those two components. Generally, the pump beam will comprise more than two frequency components, the emitted radiation also having a plurality of frequency components. Similarly, the probe beam is also preferably pulsed and comprises at least two frequency components. Generally, the pump beam and the probe beam will be derived from the same source via a beam splitter or the like.

In a tenth aspect, the present invention provides a probe for examining a sample, the probe comprising a transceiver for emitting and detecting radiation-and a dielectric member configured to direct radiation from the transceiver to the sample and to direct radiation reflected from the sample to the transceiver, wherein the transceiver is located at a focal point of the dielectric member.

Preferably the transceiver is mounted on the dielectric member.

Probes according to all aspects of the present invention comprise a dielectric member.

There are many advantages of using such a member:

If the member is solid then it gives the probe rigidity;

there is no water-vapour absorption of the THz radiation as it passes through the dielectric member;

in some embodiments, the focus is on the probing surface, thus there is no need to align or focus the probe;

there are not internal dielectric/air interfaces, hence there is reduced loss due to refection; and the high refractive index of the material can reduce the spot size of the THz radiation.

In an eleventh aspect, the present invention provides a method of examining a sample, the method comprising:

emitting a beam of emitted radiation from an emitter;

directing a said emitted beam through a dielectric medium to irradiate a sample;

directing radiation reflected from said sample using said medium into a detector;

wherein said dielectric body medium occupies at least half of the radiation path length.

BRIEF DESCRIPTION OF THE DRAWINGS

The present invention will now be described with reference to the following non-limiting embodiments in which.

DETAILED DESCRIPTION OF THE PREFERRED EMBODIMENTS OF THE INVENTION

Figure 1:
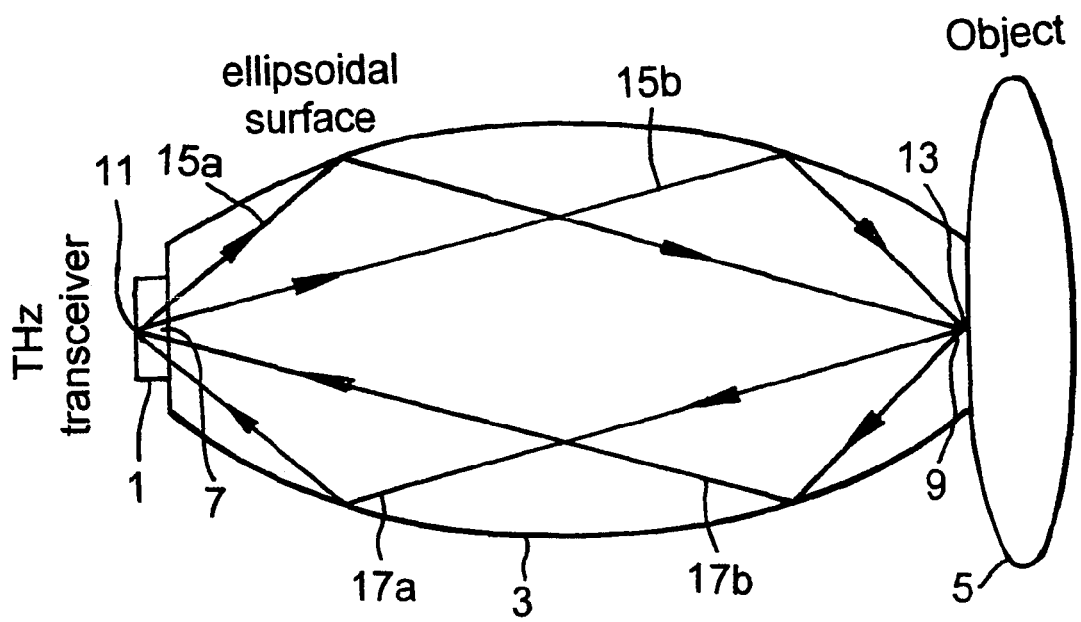
FIG. 1 shows a schematic probe with a dielectric member in accordance with an embodiment of the present invention.

The probe of FIG. 1 comprises a transceiver 1 which is connected to and abuts against elongate solid dielectric member 3. The dielectric body 3 abuts against sample 5 which is to be investigated by the probe which comprises sections 1 and 3.

The dielectric body 3 is substantially ellipsoidal in shape. The first end of the ellipse 5 is cut and transceiver 1 is provided at the first focus 9 of the ellipse. The other end 11 of the ellipse is also cut so that the second focus 13 is at the cut surface of the ellipse 15.

The dielectric member 3 is axially symmetric in that it has rotational symmetry about its long axis. In this specific example, dielectric member 3 is an ellipsoid which has been truncated to form planar surfaces 7 and 9, perpendicular to its longitudinal axis. The position of planar surface 7 is chosen such that the point of emission and detection of the transceiver 1, i.e. the actual point where THz radiation is produced of THz radiation is detected or converted into another type of signal is located at one focus 11 of the ellipsoid 3.

At the sample 5, the dielectric member 3 is truncated through the other focus 13 of the ellipsoid. Due to the geometry of the ellipsoid 3, if the transceiver 1 is positioned at one focus 11 and the sample 5 at the other 13, then radiation leaving the transceiver 1 is focused at the focal point 13 and radiation reflected from the sample 5 is focused at the transceiver 1.

The schematic path of some beams of THz radiation are shown. Paths 15a and 15b represent radiation passing from the transceiver to the sample 5 and paths 17a and 17b are the respective return paths from the sample 5 to the transceiver. The THz may propagate in either direction around the loop. Only one direction is shown here for simplicity. All the paths shown (and also those not shown) 15a, 15b, 17a, 17b are of the same length.

Figure 2:
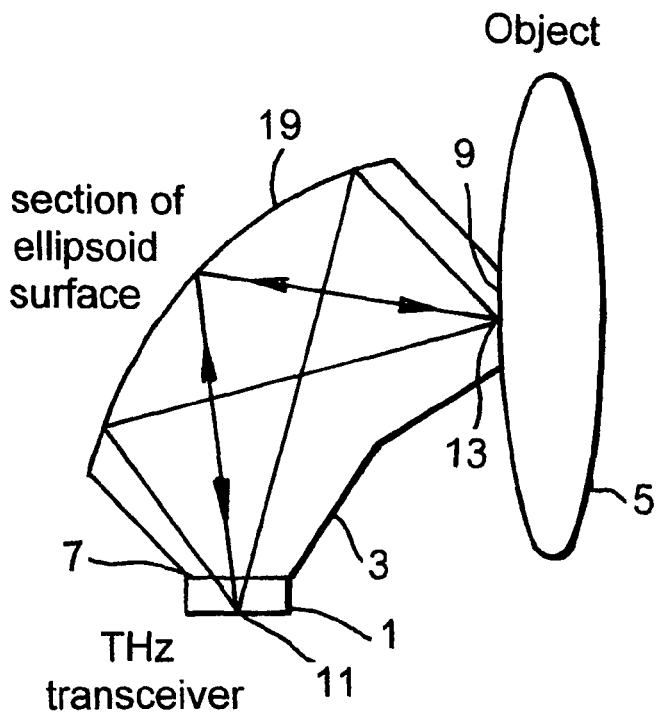
FIG. 2 shows a variation on the dielectric member of FIG. 1.

FIG. 2 shows a non-axially symmetric design. To avoid unnecessary repetition, like reference numerals will be used to denote like features.

The upper surface 19 of the dielectric body 3 is ellipsoidal. As with the dielectric body 3, of FIG. 1, the emission and detection point of the transceiver is provided at one focus of the ellipsoid and the sample 5 is provided at the other focal point of the ellipsoid. Here, there is not a full ellipse. However, the position of the focal points of ellipsoid surface 19 can still be determined. Here, its is desired for radiation entering the member 3 from transceiver 1 to irradiate a surface of sample 5 which is positioned perpendicular to the direction of emission of transceiver 1. To achieve this, the ellipsoid is cut so that the planar surface 7 which abuts transceiver 1 is perpendicular to the planar surface 9 which abuts sample 5.

The two planar surfaces 7, 9 are cleaved at 45° to the elongate axis defined by ellipsoidal surface 19. With this construction, the transceiver 1 and sample 5 can be located such that the radiation path length from the focal point of the transceiver 1 to the focal point of the sample 5 will be the same regardless of the path taken. The probe is also configured such that all radiation emitted from transceiver 1 bounces off the upper ellipsoidal surface 19 of the dielectric body 3.

Figure 3:
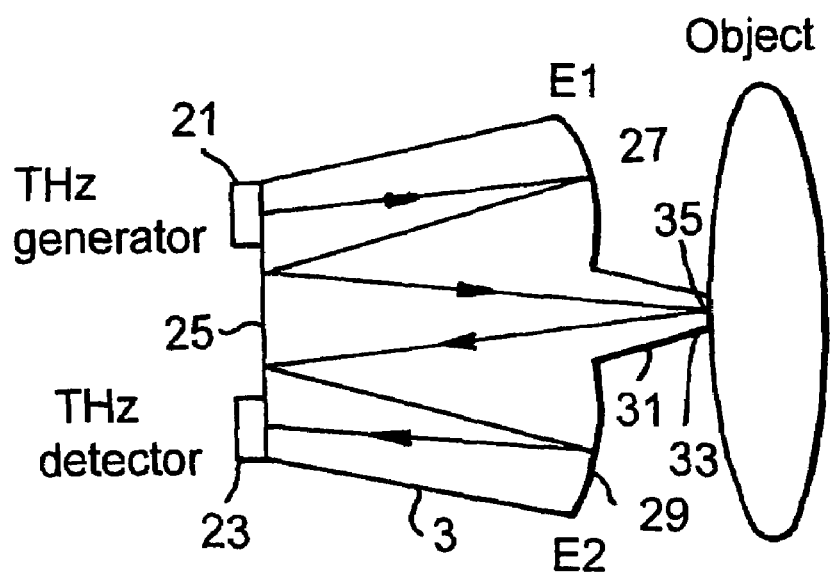
FIG. 3 shows a further embodiment of the present invention with the dielectric member configured to receive a separate THz emitter and detector.

FIG. 3 shows a further variation on the probes of FIGS. 1 and 2. Here, there is a separate THz emitter 21 and a separate THz detector 23. Both the THz emitter 21 and the THz detector 23 are mounted on dielectric member 3.

The THz emitter 21 and detector 23 are provided on planar surface 25. Opposing planar surface 25 there are formed two partial ellipsoidal surfaces 27, 29 with a projection of dielectric material 31 located between these surfaces 27, 29. One partial ellipsoidal surface 27 is provided directly opposite the emitter 21, the other ellipsoidal surface 29 is provided directly opposite the THz detector 23.

The sample 5 to be examined by the probe is positioned abutting surface 33 of protrusion 31. Radiation from emitter 21 is reflected off ellipsoidal surface 27 and onto planar surface 25, planar surface 25 then reflects the radiation down the protrusion 31 to the sample 5. Radiation reflected from the sample 5 is then reflected from the sample 5 back onto planar surface 25 and off ellipsoidal surface 29 into detector 23. Focal point 35 at the surface 33 of protrusion 31.

The radiation path length between the emitter 21 and the focal point 35, and the detector 23 and focal point 35 will remain the same regardless of the position where the beam is reflected back from ellipsoidal surfaces 27 and 29.

Figure 4:
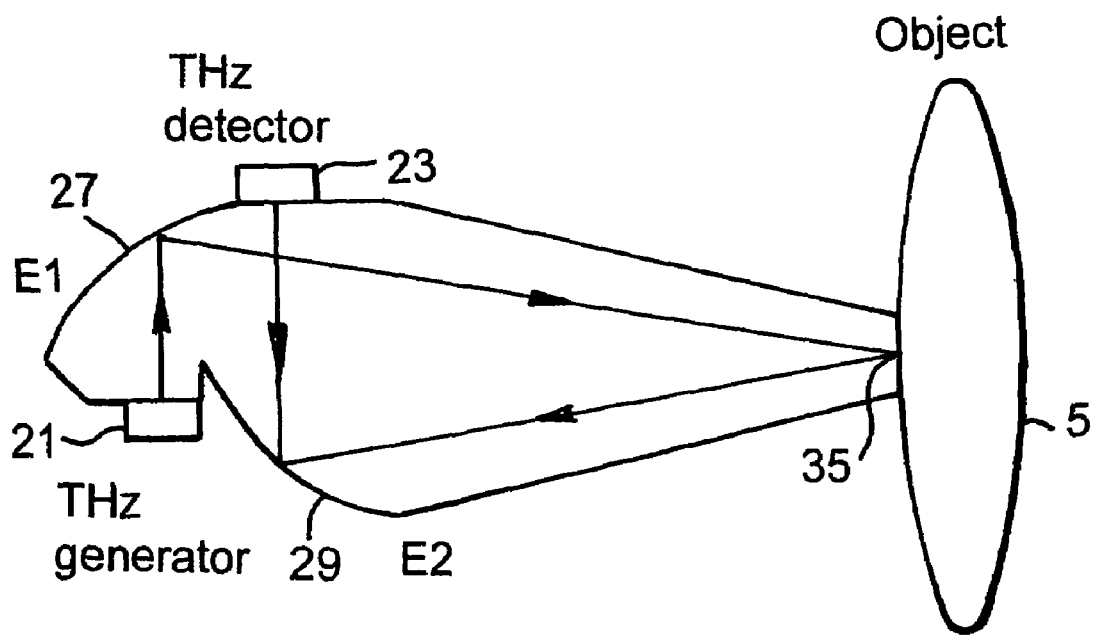
FIG. 4 shows a further variation on the embodiment of FIG. 3 having a separate THz detector and emitter.

FIG. 4 shows a further variation on the probe of FIG. 3 where the THz emitter 21 and detector 23 are separated. To avoid unnecessary repetition, like reference numerals will be used to denote like features.

The dielectric body 3 is generally elongate in shape. The sample 5 is provided at the opposing end of the dielectric member 3 to the THz emitter 21 and detector 23.

The emitter 21 is provided on the underside of member 3. Radiation from emitter 21 is reflected off partial ellipsoidal surface 27 to the focal point 35 at the sample 5. The radiation is then reflected from the sample through the dielectric body 3 back to partial ellipsoidal surface 29. Ellipsoidal surface 29 reflects the radiation back into THz detector 23 which is provided on an upper side of dielectric body 3.

Figure 5:
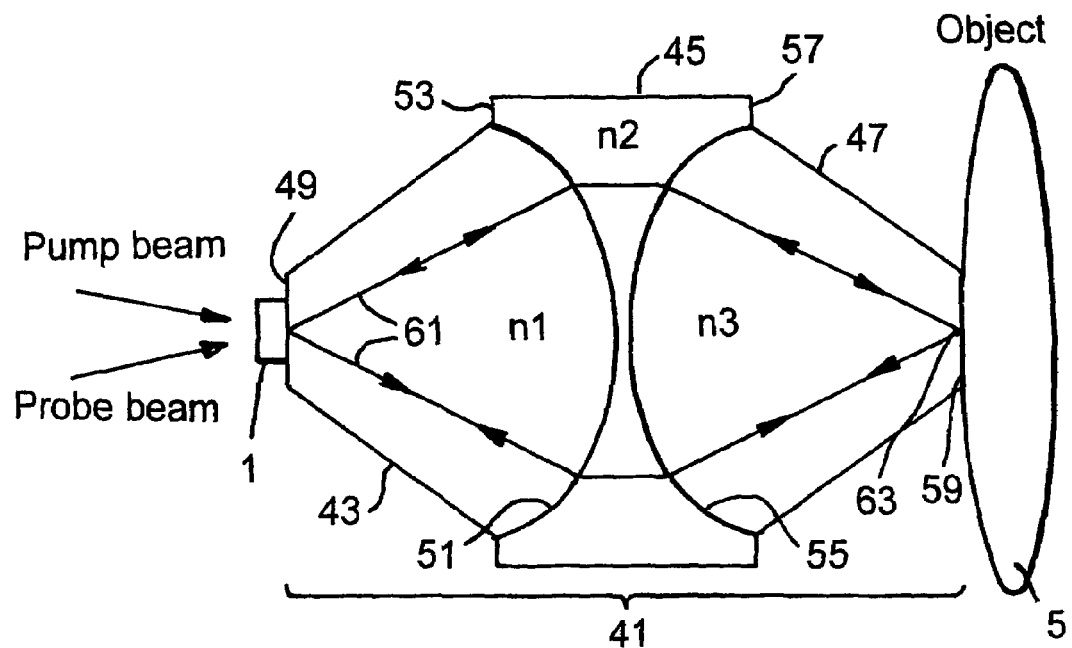
FIG. 5 shows a probe in accordance with a further embodiment of the present invention where the dielectric member has a variation in its refractive index.
Figure 6:
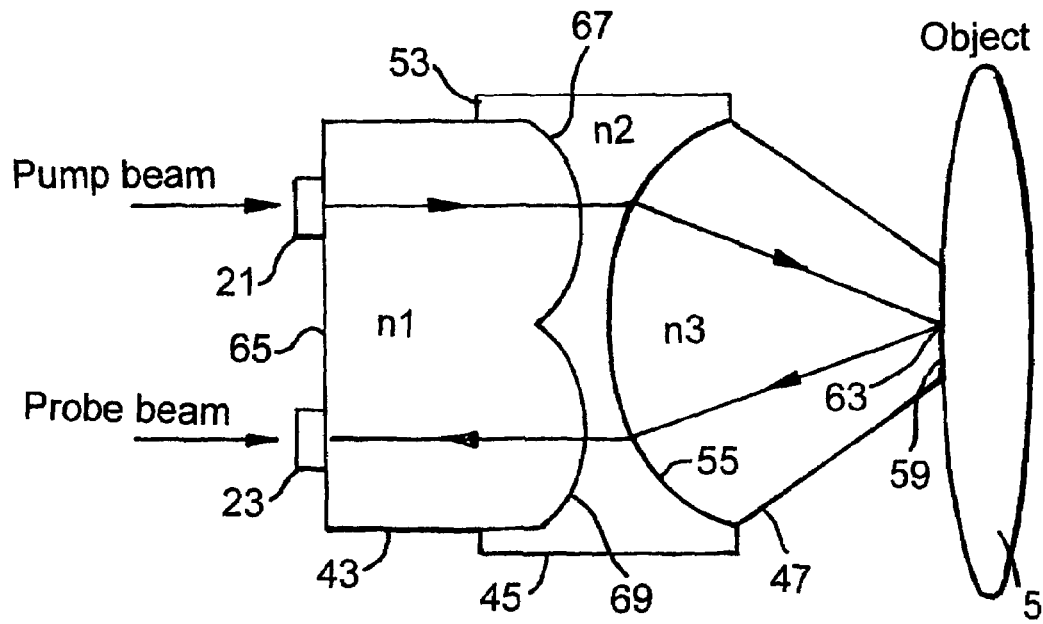
FIG. 6 shows a further variation on the probe of FIG. 5.

The above probes have directed the light between the active optical elements (i.e. the emitter 21 and detector 23) and the sample by internal reflection. In the examples of FIGS. 5 and 6, the radiation is directed by refraction.

The dielectric body 41 of the probe of FIG. 5 comprises three sections: a first section 43 to which the transceiver 1 is attached, a second middle section 45 and a third end section 47.

The first section is substantially cone shaped with a planar surface 49 for receiving the transceiver 1 and a-convex surface 51 provided opposite the planar surface 49. The convex surface 51 has a larger circumferential diameter than the planar surface 49 such that the first section 43 tapers towards transceiver 1.

The second section 45 is substantially cylindrical and the convex region 51 of the first section 43 is embedded into one of the planar sides 53 of the second section 45. The third section 47 is identical in shape to the first section 43 and is its mirror image. The third section 47 is arranged with its convex surface 55 embedded in the opposing side 57 of the second section 45 to the first section 43. The sample 5 abuts against planar surface 59 of the third section 47.

The first section 43 has a refractive index of $n_1$, the second section 45 has a refractive index of $n_2$ and the third section 47 has a refractive index of $n_3$. In the dielectric of FIG. 5, $n_2 < n_1$ and $n_2 < n_3$. Radiation being emitter from the transceiver 1 is transmitted through the first section 43 (typical paths are shown as numeral 61). The path is refracted due to the variation in the refractive index between the first 43 and second 45 sections. The beam 61 is then further refracted at the interface between the second 45 and third 47 sections and the radiation is focused onto the focusing point 63 of the surface 59. In this example, the second section 45 forms a bi-concave lens.

If the refractive index of the second section 45 is higher than the first 43 and third 47 sections, then the second section 45 should be formed as a bi-convex lens, the convex surfaces of the first and third sections 51, 55 being replaced by concave surfaces.

The second section 45 may be formed from polythene, paraffin wax, silicon, silica, TPX, polypropylene or another material which is largely transparent to radiation in the terahertz regime. Composite materials such as dielectrically loaded epoxy or plastic might also be useful. A liquid dielectric could also be used such as silicone grease or fluid or liquid paraffin. If a liquid dielectric is used, an further device (not shown) should also be used to provide rigidity and support for the components as well as sealing the fluid in place.

FIG. 6 shows a modification of the probe of FIG. 5. -Here, a separate emitter 21 and detector 23 are used. The first section 43 comprises a planar surface 65 which abuts against the emitter 21 and the detector 23. The emitter 21 and detector 23 are spaced apart from one another on the surface 65.

A convex surface 67 is provided opposite the emitter 21 and is positioned such that the emitter 21 is directly opposite the centre of this surface 67. A second convex surface 69 is provided opposite the detector 23 such that the detector 23 is directly opposite the centre of the surface 69. The two convex surfaces 67, 69 of the first section 43 are embedded into one of the planar sides 53 of the second section 45 in the same manner as described with reference to FIG. 5.

The third section 47 and the remainder of the second section 45 are the same as those described with reference to FIG. 5.

The three sections 43, 45, 47 are configured such that radiation emitted from the emitter 21 is refracted and focused onto focal point 63. Radiation collected from focal point 63 is directed by refraction back into detector 23.

Figure 7:
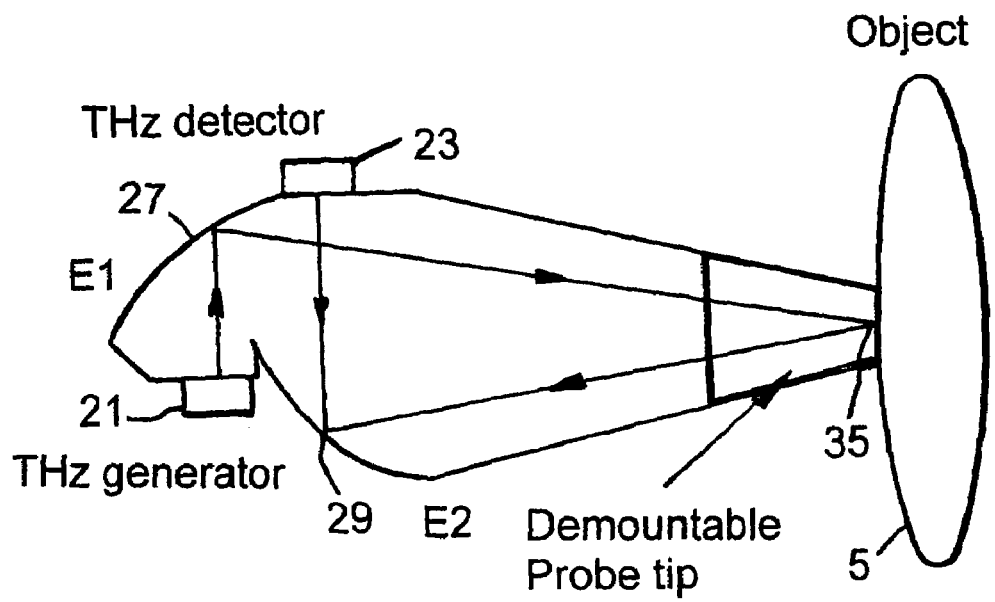
FIG. 7 shows a further embodiment of the present invention having a dielectric member with a demountable tip.

FIG. 7 shows a variation of the probe of FIG. 4. The sample end of the elongate dielectric body 3 is referred to as the probe tip 71. In FIG. 7, this is demountable and remountable from the remainder of the dielectric body 3. The demountable tip 71 can be fixed to the remainder of the dielectric body 3 by a mechanical clip or clamp and preferably by a spring-loaded clip. Alternatively, the demountable tip 71 could be affixed using glue.

In FIG. 7, the demountable tip 71 is made from the same material as the remainder of the dielectric body 3 as there is no refraction of the emitted THz beam as the beam enters the tip. However, the tip 71 could also be made from a different material.

Figure 8:
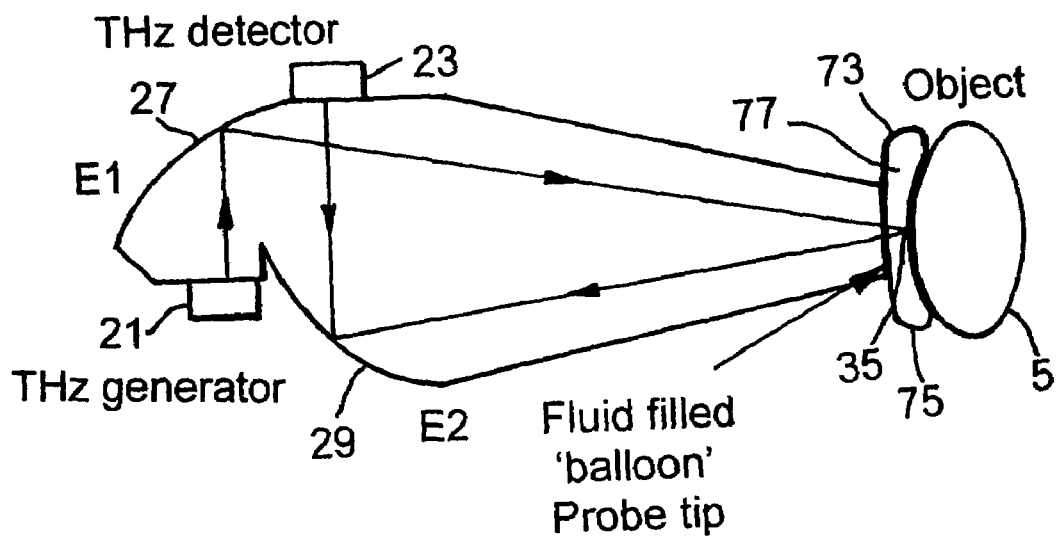
FIG. 8 shows a probe in accordance with a further embodiment of the present invention having a dielectric member which is attached to a fluid filled "balloon" probe tip.

FIG. 8 shows the probe of FIG. 4 with a different type of tip. The tip 73 comprises a balloon type structure 75 which is filled with a fluid 77 which is substantially transparent to THz radiation. The balloon 75 can be formed from polythene, silicone rubber, the fluid 77 can be silicone fluid, mineral oil or wax. The tip 71 is configured to mould to the shape of non-planar surfaces, for example, teeth, so that a good contact can be made.

The balloon 75 could be affixed to the dielectric body 3 using a thin layer of adhesive which is substantially transparent to THz radiation. For example, superglue, epoxy, acrylic, etc. adhesives could be used. Wax could also be used. Wax is particularly advantageous as it could be melted to remove the tip. Alternatively, balloon 75 could be attached by clipping it around the edge of dielectric body 3.

Figure 9:
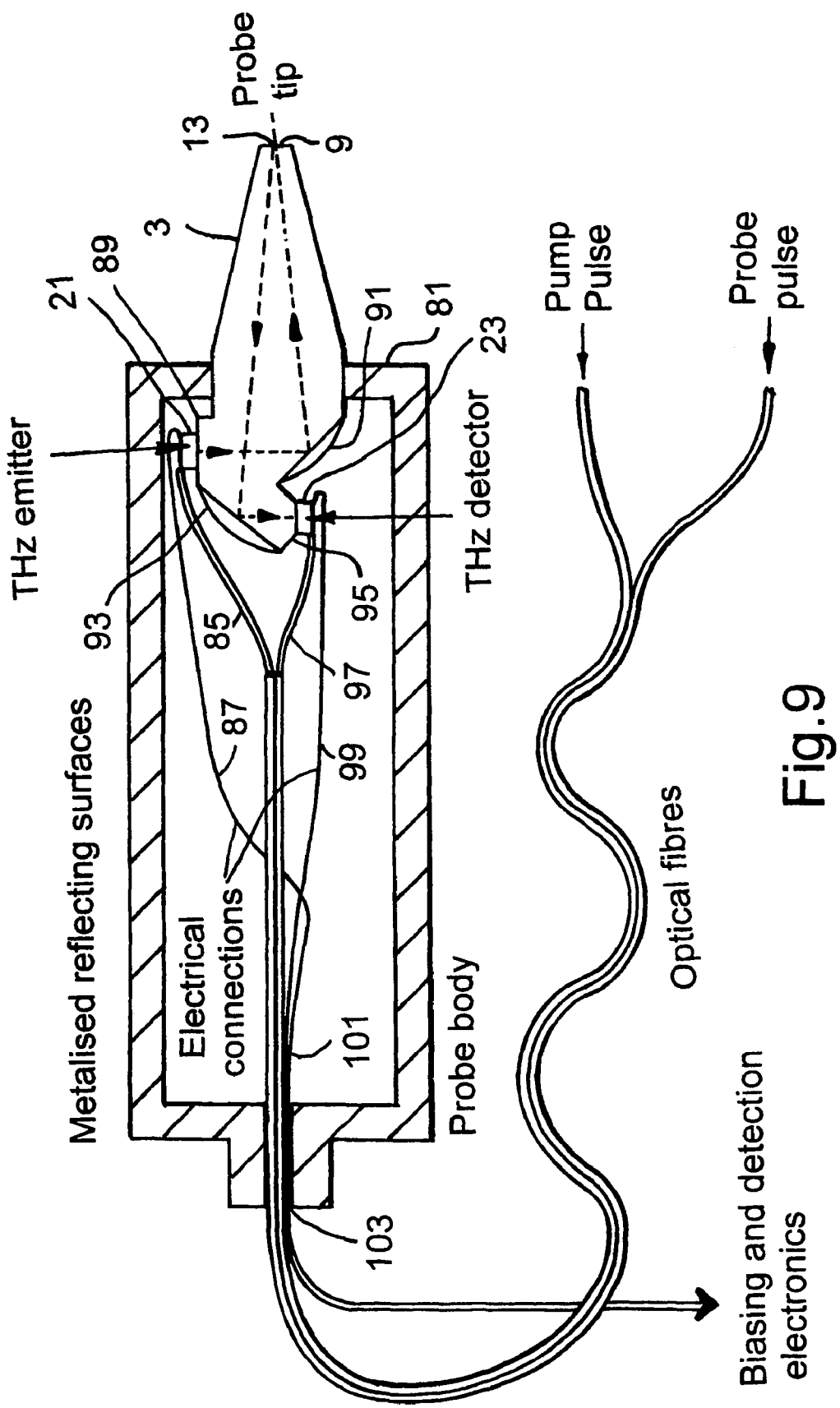
FIG. 9 shows a THz probe in accordance with an embodiment of the present invention.

FIG. 9 is a schematic of a probe assembly with housing. The dielectric body 3 is the same as that described with reference to FIG. 4 and a detailed description will not be repeated here. The dielectric body 3 is mounted at the distal end 81 of a probe housing 83. The dielectric body 3 protrudes outside the housing 83 such that the probing surface 9 of the dielectric body 3 is remote from the probe housing 83. The positions for receiving the emitter 21 and the detector 23 on the dielectric body 3 are located within the probe housing 83.

In this example, photo-conductive antennas are used to both emit and detect THz radiation. The emitter comprises a photo-conductive material having a pair of surface electrodes formed thereon with a gap therebetween. Applying a suitable bias across the electrodes and irradiating the photo-conductive material between the electrodes with radiation having a suitable frequency (a pump beam) results in the emission of radiation in the THz regime.

The pulsed radiation required in order for the emitter to generate THz radiation is supplied via fibre optic cable 85. The bias which is to be applied to the electrodes of the photo-conductive antenna is provided via electrical cable 87.

The emitter 21 is located at emitter receiving surface 89 which is located opposite partial ellipsoidal surface 91 on the dielectric body 3. Ellipsoidal surface 91 is coated with metal in order to enhance its reflective properties. Ellipsoidal surface 91 reflects all radiation from the emitter to the focal point 13 on the probing surface 9.

Radiation which is reflected from the sample under investigation (not shown) at the focal point 13 is reflected back into the dielectric body 3 and onto partial ellipsoidal surface 93. This surface 93 reflects radiation from the sample into the THz detector 23 which is located on detector receiving surface 95 of the dielectric body 3.

The detector 23 is structurally the same as the emitter except that it works in the inverse manner. The same radiation which is supplied to the emitter in order to generate THz radiation is supplied to the detector via optical fibre cable 97 as a probe beam. When THz radiation is incident on the detector with the probe beam a photocurrent is generated between the two electrodes. Measurement of this photocurrent-allows magnitude and phase information of the THz radiation reflected from the sample to be measured. The photocurrent is carried away from the probe using electric wire 99.

The optical fibres 85, 97 which carry the input beams to the emitter 21 and detector 23 and the electrical wires 87, 99 which carry electrical signals to the emitter and from the detector are bundled together to form umbilical fibre 101 which exits the probe housing 83 at fibre insert point 103, which is located in the opposing side of the housing-83 to the dielectric body 3.

Figure 10:
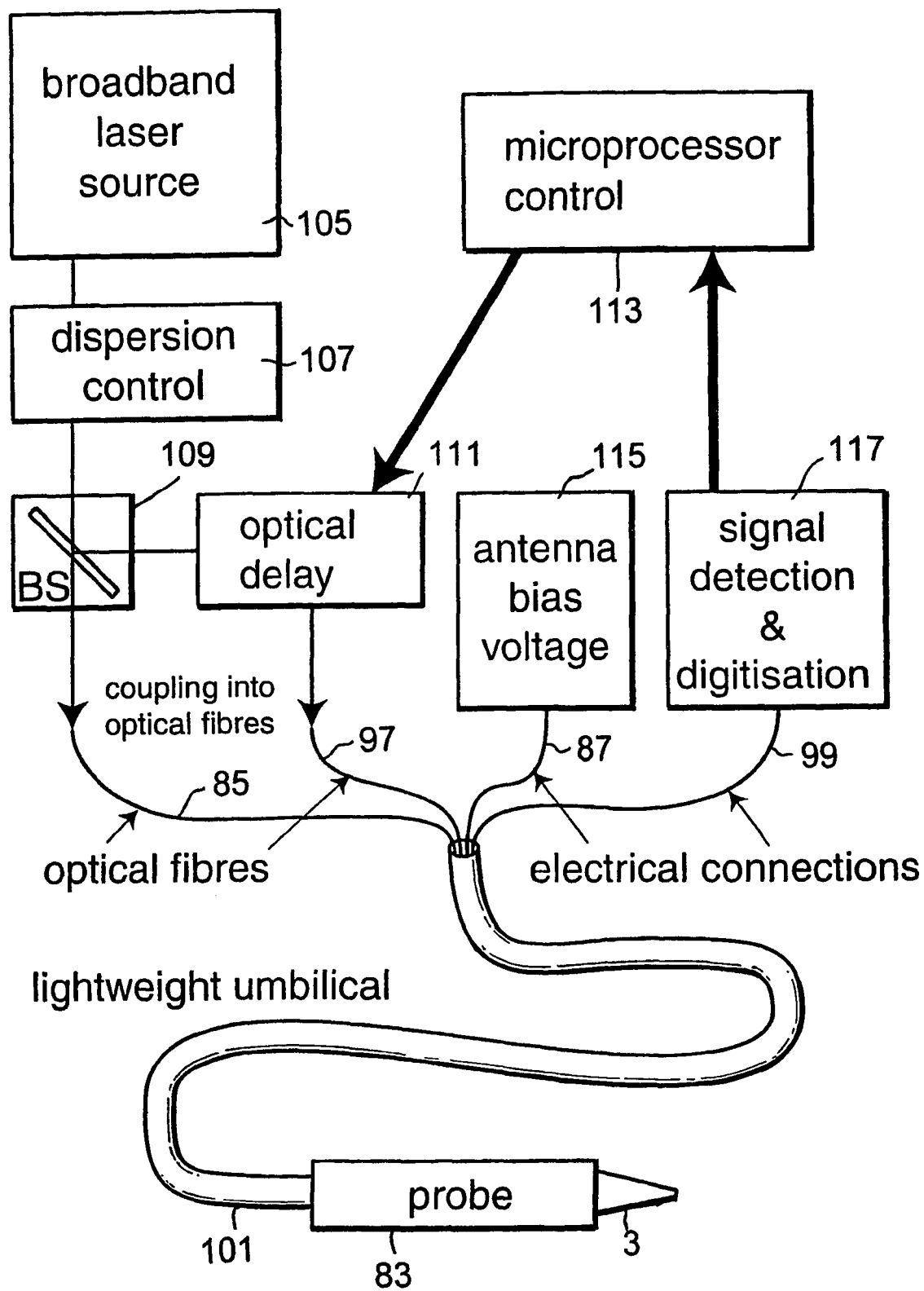
FIG. 10 shows a block diagram of the control system for a probe in accordance with the present invention.

The overall system is shown schematically in FIG. 10. Here, umbilical fibre 101 is shown connected to the probe housing 83 and to the control optics and electronics.

First, the optical inputs 85 and 97 to the probe will be described. Broad band laser source 105 provides the pump beam (the input beam for the emitter) and the probe beam (the input beam for the detector). The output from the laser 105 is fed into a dispersion controller 107 in order to precompensate for the dispersion which occurs in the fibre. The Pulse from the dispersion controller 107 is then directed into beam splitter 109, where the beam is split into a pump beam 85 which is transmitted directly to the emitter (21—of FIG. 9) and a probe beam 97.

The probe beam 97 is fed into optical delay line 111 which is controlled by microprocessor 113. The optical delay line 111 has a range of ±30 cm and operates at a frequency of about 0.000 Hz to 500 Hz and sweeps the delay of the probe pulse back and forth in time so that the phase of the probe beam can be matched to the THz beam received at the detector 23. Typically, the delay line is scanned over a range of ±4 mm and at a frequency of 20 Hz. The probe beam is then directed to the detector in the probe using a fibre optic cable 97.

An emitter bias voltage is provided by unit 115, this biases one of the electrodes of the emitter with respect to the other electrode in order to emit a radiation having a frequency in the THz frequency range upon irradiation with the pump pulse.

The electrical signal detected by the detector is fed back into an electrical signal detector and digitiser 117 via wire 99. The output of the electrical signal detector and digitiser 117 is then fed to the controller 113 which also controls the optical delay line 111.

Figure 11:
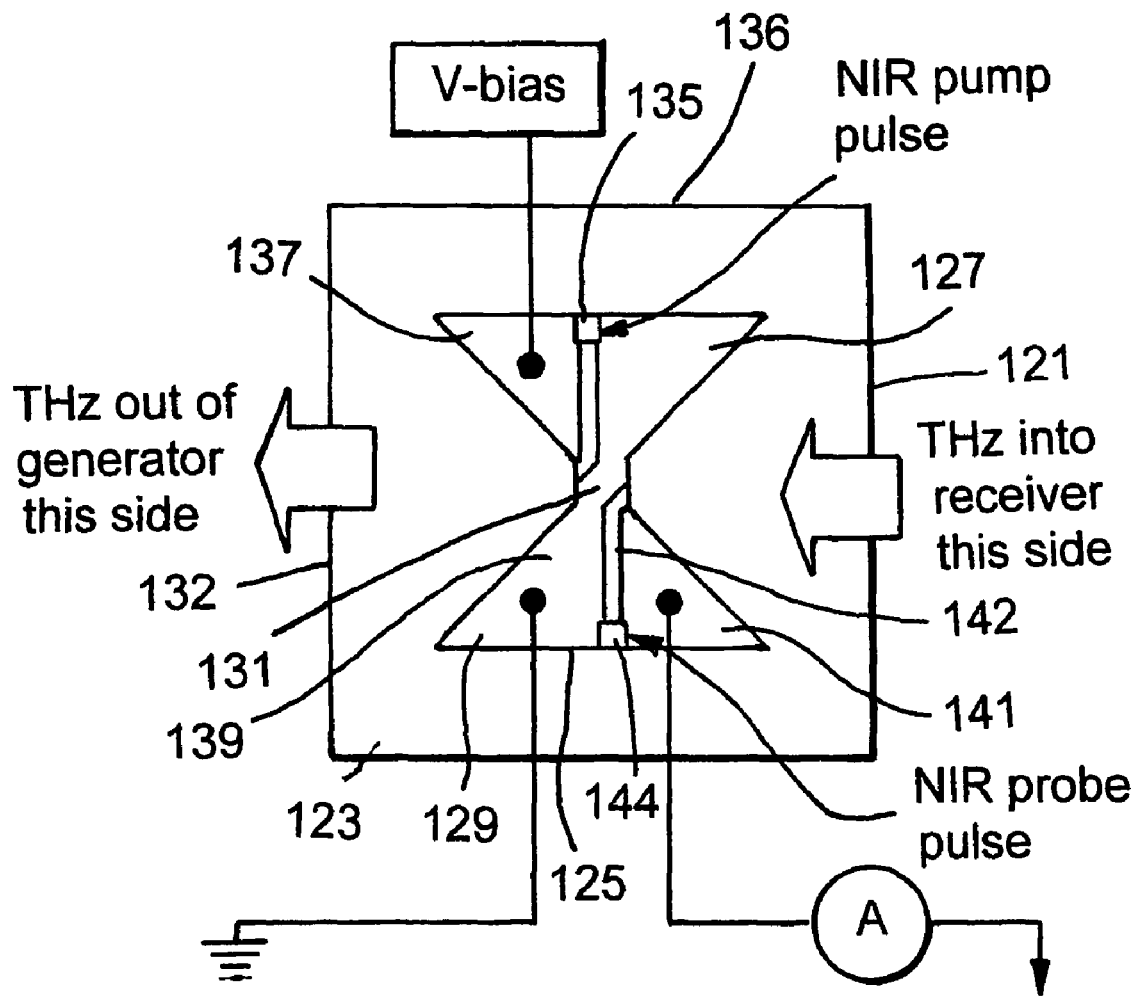
FIG. 11 shows a transceiver in accordance with an embodiment of the present invention.

The above has been described in detail with reference to a separate emitter and detector. However, a transceiver which both emits and detect THz radiation can be used. Such a transceiver is shown in FIG. 11.

The transceiver 121 comprises a substrate 123 such as sapphire, GaAs, Si, Ge, Quartz etc. A surface electrode 125 is provided overlying the substrate 123. The surface electrode 125 forms a bow-tie structure having two triangles 127, 129 joined at an apex 131 to form waist 132 of the electrode 125.

The upper triangle 127 of the electrode 125 has a longitudinal gap 135 formed through it such that one part 137 of this triangle is separated from the remainder of the upper triangle 127. First gap 135 extends from waist 132. First photoconductive member 136 is located in the first gap 135 and at its furthest end from waist 132, to bridge the gap 135 between the two parts 127, 135 of the upper triangle.

The lower triangle 129 is also configured in the same way and has a second longitudinal gap 142 formed through it such that one part 141 of this triangle is separated from the remainder of the lower triangle 129. Second gap 141 extends from waist 132. Second photoconductive member 144 is located in the second gap 141 and at its furthest end from waist 132, to bridge the gap 141 between the two parts 129, 141 of the lower triangle.

First and second photoconductive members can comprises radiation damaged silicon or low temperature GaAs, Arsenic implanted GaAs or any other semiconductor.

Therefore, the electrode comprises three separated sections, a central section 139 which is formed from two partial triangles joined at their apex and two separate triangular sections 137, 141 located on either side of the central section. The upper triangle 127 in this example acts as a THz emitter and the lower triangle 129 works as a THz detector.

In the upper triangle 127, a bias is applied between the upper isolated section 137 and the central section 139 which is grounded, thus, a bias is applied across first photoconductive member 136. Irradiating the first photoconductive member 136 when the bias is applied with a near infrared pump pulse, of about 800 nm, causes the flow of surface carriers between the isolated section 137 and central section 139 of the upper triangle 127 which in turn generates radiation having a frequency in the THz regime. First gap 135 acts a transmission line and the THz radiation is guided along gap 135 until it reaches waist 132. The THz radiation is then emitted from waist 132.

To detect THz radiation, the lower triangle 129 is used. A near infrared probe pulse is used to illuminate the photoconductive material between the isolated section 141 and central section 139 of the lower triangular electrode 129. THz radiation approaching the device from the right hand side is focused onto waist 132 and propagates along gap 142 to second photoconductive member 144. This causes a current flow through the second photoconductive member 144 between the central section 139 and the isolated section 141 of the lower triangular electrode 129.

Figure 12A:
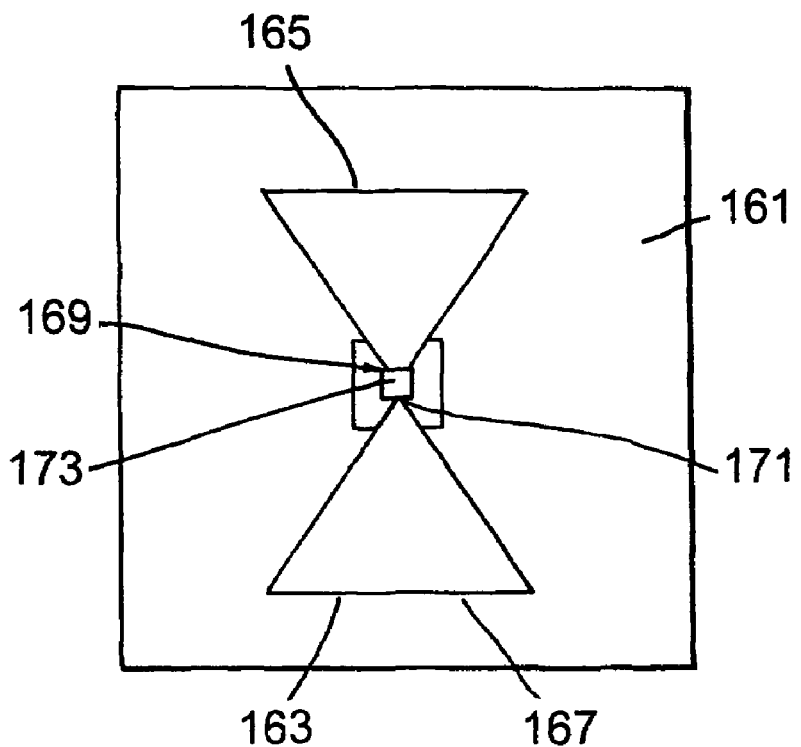
FIGS. 12a and 12b shows a transceiver in accordance with an embodiment of the present invention.
Figure 12B:
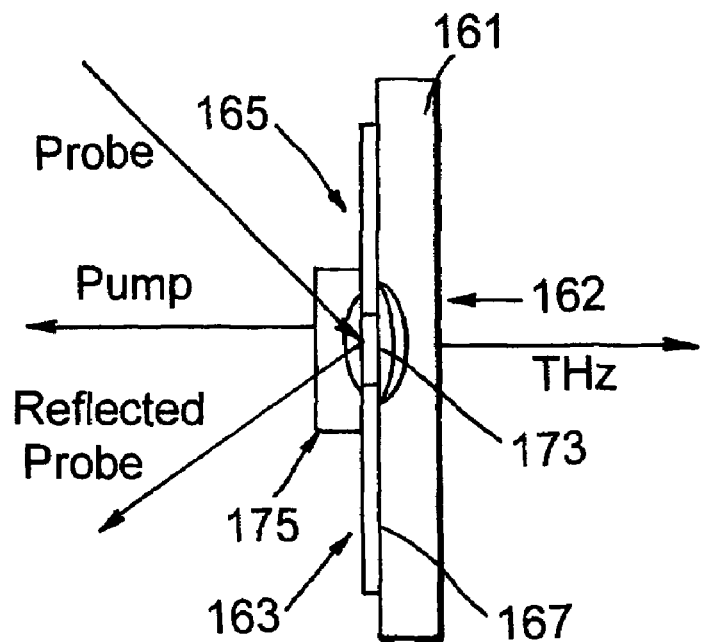

FIGS. 12a and 12b illustrates a further type of transceiver in accordance with an embodiment of the present invention. FIG. 12a is a plan view and FIG. 12b is a side view.

The transceiver comprises a substrate 161 which may be sapphire, GaAs, Si, Ge etc. A bow-tie electrode 163 formed from gold is provided overlying the surface of the substrate. The bow tie electrode, comprises an upper triangle 165 and a lower triangle 167, which are arranged with a pair of apexes 169, 171 (one from each triangle) facing one another. The facing apexes are spaced apart and a photo conducting member 173 bridges the gap between the two apexes 169, 171. The photoconducting member 173 may comprise radiation damaged silicon, low temperature growth GaAs etc. The photoconducting member may be electrically isolated from the substrate.

A non linear member 175 is then provided overlying the photoconductive member 173 and part of the electrodes. The non-linear material preferably comprises ZnTe, GaAs, GaP, GaSe or any material which has strong second order non-linearity.

The photoconductive member 173 primarily serves to generate THz radiation, the non-linear member 175 generally serves to detect THz radiation.

THz radiation is generated in response to irradiating the transceiver with a pump pulse. A bias is applied across the photoconducting member using the two triangular electrodes 165, 167. The pump pulse passes through the non-linear member 175 and irradiates the photoconducting member causing the emission of THz radiation. The radiation is directed into the region with the highest refractive index, thus the THz radiation is emitted through substrate 161 and emerges out of the substrate on the opposite side 162 to electrodes 165, 167.

THz radiation received by the transceiver is collected at the point between the apexes of the triangles 165, 167 and photoconducting member 173. The field of the collected THz radiation also extends into non-linear member 175. The THz radiation can then be detected using an electro-optic sampling technique as the THz radiation incident on the non-linear member 175 will rotate the polarisation of a probe pulse incident on the non-linear material 175. Electro-optic sampling techniques are well known in the art and are explained in GB 2 343 964.

The above has described the use of non-linear member 175 as a detector and photoconducting element 173 as an emitter. However, their roles could be reversed and THz could be detected by measuring the current induced in the photoconducting element 173 (as opposed to measuring the rotation of the polarisation of the probe pulse) and the non-linear member 175 can be used to emit THz radiation.

In the previous examples, the optically active element, whether it be an emitter, detector or transceiver, is fitted to the dielectric body. Ideally, such an element should be fitted so that it is rigidly connected to the dielectric body so that it cannot rotate with respect to the dielectric body.

Figure 13:
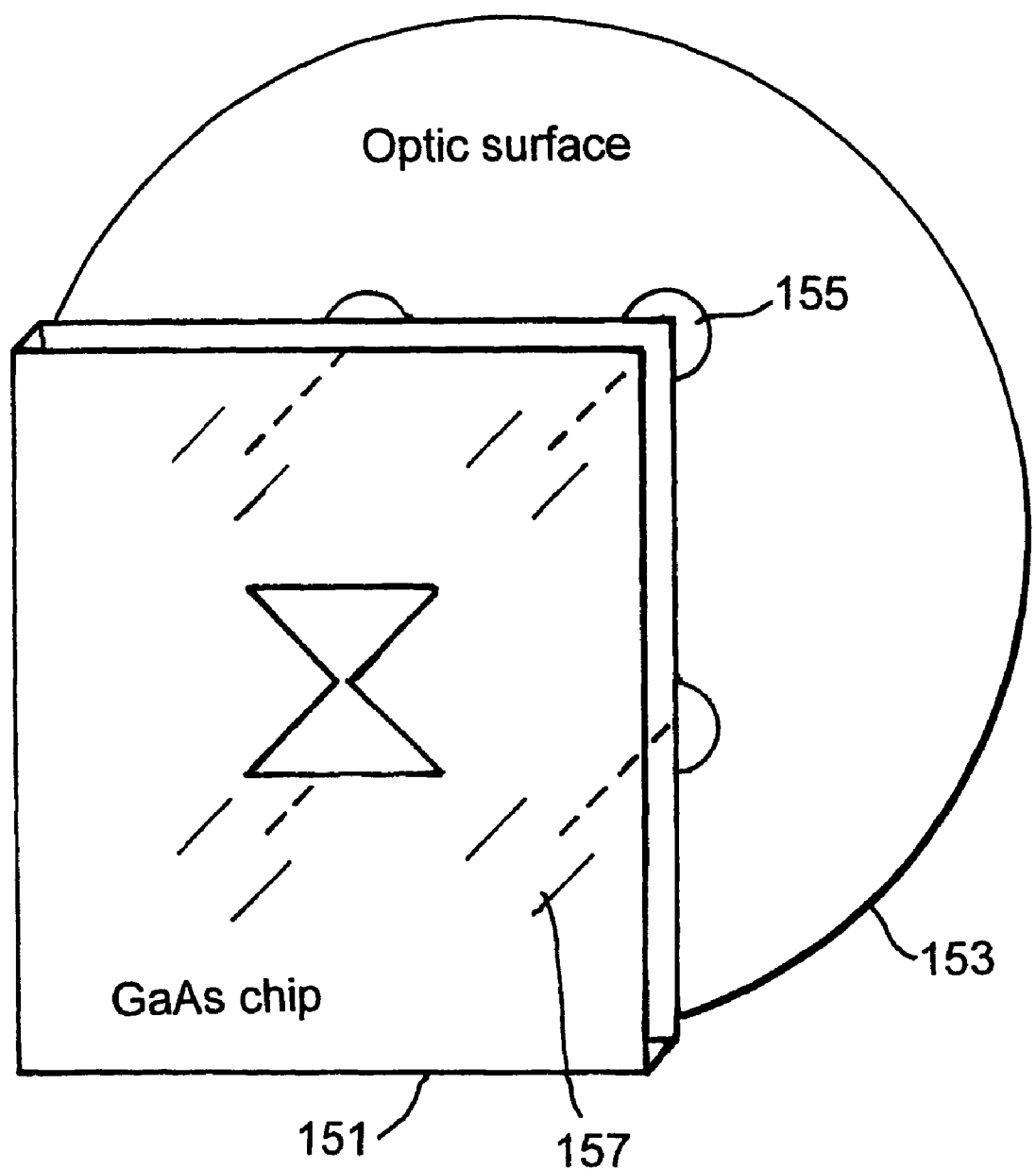
FIG. 13 shows a means for attaching a transceiver, detector or emitter to the dielectric member of a probe in accordance with an embodiment of the present invention.

An example of a method of fitting an optically active element 151 onto a dielectric body 153 is shown in FIG. 13. Here, a plurality of alignment holes 155 are drilled, or machined or etched into the dielectric body 153 using CNC machining techniques.

A matching set of alignment mesas 157 are provided on the side of the active element which abuts the dielectric. The mesa can be formed using photolithography and conventional deep etching techniques. The mesa pattern 157 on the optically active element 151 can then be aligned precisely with the holes 155 of dielectric element 153 using standard through-wafer alignment and fabrication techniques. The optically active element 151 is then fitted on the dielectric by fitting the mesa 157 into the holes 155.

Of course, the holes could be formed in the optically active element 151 and the mesa could be formed in the dielectric body 153.

The invention claimed is:

1. A probe for examining a sample, the probe comprising an active optical element for emitting and/or detecting radiation and a dielectric member for transmitting the radiation between the sample and the active element, wherein the active element is mounted on the dielectric member at a focal point and wherein the dielectric member comprises a container and a non-rigid material provided within the container.

2. The probe of claim 1, wherein the non-rigid material is chosen from silicone grease, silicone fluid, liquid paraffin, mineral oil, particulate loaded fluid or colloid.

3. A probe for examining a sample, the probe comprising first and second optically active elements, wherein the first optically active element is an emitter having at least one frequency in the range from 25 GHz to 100 THz and the second optically active element is a detector, and the probe further comprises a dielectric member for transmitting the radiation from the first optically element to a sample under examination to irradiate the sample and for transmitting radiation reflected from the sample under examination to the second optically active element, wherein the first and second optically active elements are mounted at focal points on the dielectric member.

4. A probe for examining a sample, the probe comprising first and second optically active elements, wherein the first optically active element is an emitter having at least one frequency in the range from 25 GHz to 100 THz and the second optically active element is a detector, and the probe further comprises a dielectric member for directing the radiation from the first optically active element to a sample under examination to irradiate the sample and for directing radiation reflected from the sample under examination to the second optically active element, wherein the dielectric member provides substantial structural rigidity to the probe, the first and second optically active elements being located at focal points of the dielectric member.

5. The probe of claim 4 wherein the emitter is spatially separated from the detector.

6. The probe of claim 4, wherein the first optically active element is located such that radiation passes from the first optically active element to the dielectric member without passing through free space or an air gap.

7. The probe of claim 4 wherein the first optically active element abuts against a surface of the dielectric member such that radiation passes from the first optically active element to the dielectric member without passing through free space or an air gap.

8. The probe of claim 4, wherein the dielectric member has a probing surface through which radiation from the first optically active element exits the dielectric member to irradiate the sample and radiation reflected from the sample enters the dielectric member.

9. The probe of claim 8, wherein the probing surface is configured to abut against the sample under investigation.

10. The probe of claim 4, wherein the dielectric member is configured to direct the radiation by internally reflecting the radiation within the member.

11. The probe of claim 4, wherein the dielectric member comprises at least two sections.

12. The probe of claim 11, wherein the at least two dielectric sections have differing refractive indices.

13. The probe of claim 11, wherein the dielectric member comprises first, second and third sections, arranged such that radiation emitted from the first optically active element passes through the first section, then the second section and then the third section prior to irradiating the sample.

14. The probe of claim 13, wherein the second section is formed from one chosen from polythene, paraffin wax, silicone, silica, TPX or polypropylene.

15. The probe of claim 13, wherein the second section comprises a container and a non-rigid material provided within the container.

16. The probe of claim 4, wherein at least a section of the dielectric member comprises crystalline silicon, amorphous silicon, amorphous germanium, crystalline germanium, quartz, sapphire, diamond, high density polythene, TPX or alumina.

17. The probe of claim 4, wherein the first optically active element is configured to emit pulses of radiation having a plurality of frequencies, at least one of said frequencies being in the range from 25 GHz to 100 THz.

18. A probe according to claim 4, wherein the member comprises at least two sections having different refractive indices.

* * * * *